(12) United States Patent
Moriuchi et al.

(10) Patent No.: US 8,900,628 B2
(45) Date of Patent: Dec. 2, 2014

(54) HARD CAPSULE AND METHOD FOR PRODUCING SAME

(75) Inventors: Toshiaki Moriuchi, Yamatokoriyama (JP); Akane Kojo, Kyoto (JP); Yusuke Hayashi, Kobe (JP); Hiroyuki Yoshino, Kobe (JP)

(73) Assignee: Nisshin Kasei Co., Ltd., Osaka-shi (JP)

( * ) Notice: Subject to any disclaimer, the term of this patent is extended or adjusted under 35 U.S.C. 154(b) by 0 days.

(21) Appl. No.: 13/581,022

(22) PCT Filed: Feb. 25, 2011

(86) PCT No.: PCT/JP2011/054251
§ 371 (c)(1),
(2), (4) Date: Aug. 24, 2012

(87) PCT Pub. No.: WO2011/105534
PCT Pub. Date: Sep. 1, 2011

(65) Prior Publication Data
US 2012/0316250 A1 Dec. 13, 2012

(30) Foreign Application Priority Data
Feb. 26, 2010 (JP) ................. 2010-043429

(51) Int. Cl.
*A61K 9/48* (2006.01)
*A61J 3/07* (2006.01)

(52) U.S. Cl.
CPC ............... *A61J 3/077* (2013.01); *A61K 9/4891* (2013.01); *A61K 9/4816* (2013.01)
USPC ........................................................ 424/452

(58) Field of Classification Search
None
See application file for complete search history.

(56) References Cited

U.S. PATENT DOCUMENTS

2003/0166763 A1* 9/2003 Hoshi et al. .................. 524/459
2005/0186268 A1 8/2005 Hoshi et al.
2011/0280937 A1 11/2011 Moriuchi et al.
2012/0022169 A1 1/2012 Moriuchi et al.

FOREIGN PATENT DOCUMENTS

| JP | 2001-170137 A | 6/2001 |
| JP | 2005-170929 A | 6/2005 |
| JP | 2006-289711 A | 10/2006 |
| WO | WO-02/17848 A1 | 3/2002 |
| WO | WO-2009/125483 A1 | 10/2009 |
| WO | WO-2009/125485 A1 | 10/2009 |
| WO | WO-2010/093020 A1 | 8/2010 |
| WO | WO-2010/114134 A1 | 10/2010 |

OTHER PUBLICATIONS

Tako et al., Molecular origin for rheological characteristics of native gellan gum, Colloid Polym Sci (2009) 287:1445-1454.*

(Continued)

*Primary Examiner* — Anand Desai
*Assistant Examiner* — Melissa Mercier
(74) *Attorney, Agent, or Firm* — Edwards Wildman Palmer LLP

(57) ABSTRACT

This invention provides a hard capsule that has excellent stability even when filled with a solvent for dissolving poorly soluble drugs, and that also achieves reduction in disintegration time, thereby ensuring excellent solubility.

Specifically, the hard capsule of the present invention has a film comprising:

(A) a polymer or copolymer obtained by polymerizing or copolymerizing, in the presence of polyvinyl alcohol and/or a derivative thereof, at least one polymerizable vinyl monomer represented by Formula (1):

$$H_2C=C(R^1)-COOR^2 \qquad (1)$$

wherein $R^1$ represents hydrogen or methyl, and $R^2$ represents hydrogen or alkyl having 1 to 4 carbon atoms; and (B) native gellan gum.

5 Claims, 1 Drawing Sheet

(56) References Cited

OTHER PUBLICATIONS

Tako et al., Molecular Origin for rheological characteristics of native gellan gum, 2009.*

W. J. Bowtle, "Liquid Filling of Hard Gelatin Capsules: A New Technology for Alternative Formulations," Pharmaceutical Technology Europe, Oct. 1998, pp. 84, 86, and 88-90.

International Search Report dated Apr. 5, 2011, issued for PCT/JP2011/054251.

* cited by examiner

HARD CAPSULE AND METHOD FOR PRODUCING SAME

The present invention relates to a hard capsule comprising a film, which comprises a copolymer and a specific compound. The copolymer is obtained by copolymerizing polyvinyl alcohol and/or a derivative thereof and at least one polymerizable vinyl monomer. The present invention also relates to a production method of the hard capsule.

BACKGROUND ART

Many of the active substances of medicines, i.e., pharmaceutical active ingredients, have poor water solubility. Such substances are poorly absorbed from the alimentary tract, and the bioavailability and drug efficacy expression are easily reduced or are subject to fluctuation. For this reason, in pre-clinical tests that evaluate drug efficacy or obtain biopharmaceutical parameters using lab animals or the like, the pharmaceutical active ingredients are often dissolved in some solvent to make them more easily absorbed. For a poorly soluble pharmaceutical active ingredient, it is possible to use a polyethylene glycol having relatively low molecular weight and a derivative thereof, a polyoxyethylene sorbitan fatty acid ester, a fatty acid having 6 to 12 carbon atoms or a salt thereof, polyoxyethylene castor oil, a diethylene glycol derivative, or the like. However, these solvents are usually in liquid form and not easily processed into tablets. Therefore, it is necessary to consider the ultimate dosage form of these solvents for sale in the market. If these solvents could be directly formulated into pharmaceutical preparations, the time required for formulation could be greatly shortened. A capsule is highly anticipated to serve as such a dosage form.

Capsules hitherto known are those produced using gelatin or a cellulose derivative as a base material. When a known gelatin hard capsule is filled with a polyethylene glycol having a weight average molecular weight of 400 (PEG 400), the moisture in the capsule film migrates into the solvent, causing the capsule to break (see Non-Patent Literature (NPL) 1). Moreover, in known cellulose derivative-based capsules, the aforementioned solvents act as plasticizers, causing them to, for example, permeate the capsule film and be exuded to the capsule surface.

In order to solve such problems, Patent Literature (PTL) 1 discloses a hard capsule comprising a film that comprises a specific polyvinyl alcohol copolymer and polyvinyl alcohol. This hard capsule has improved fracture resistance and impact resistance. However, because of the low solubility of polyvinyl alcohol particularly under a low temperature, it takes a long time to dissolve this hard capsule. Therefore, the capsule was not suitable to contain, in particular, medicaments that must be quickly absorbed.

CITATION LIST

Patent Literature

PTL 1: Pamphlet of WO 2009/125483
PTL 2: Pamphlet of WO 2002/017848

Non-Patent Literature

NPL 1: Pharmaceutical Technology Europe, October, 84, 86, 88-90, 1998

SUMMARY OF THE INVENTION

Technical Problem

The principal object of the present invention is to provide a hard capsule that has excellent stability when filled with a solvent for dissolving poorly soluble drugs (hereinafter also referred to as a poor-solubility-drug-dissolving solvent), and that also achieves reduction in disintegration time, thereby ensuring excellent solubility.

Solution to Problem

The present inventors conducted extensive research to achieve the above object and found that a hard capsule produced by incorporating native gellan gum into a polymer or copolymer obtained by polymerizing or copolymerizing at least one polymerizable vinyl monomer in the presence of polyvinyl alcohol and/or a derivative thereof has excellent stability even when filled with a solvent for dissolving poorly soluble drugs, and it also achieves reduction in disintegration time, thereby ensuring excellent solubility. The present inventors further found that such a hard capsule also achieves excellent mechanical strength and suppression of film softening in a low-humidity environment. The present inventors further found that the mechanical strength can be further improved by producing the capsules by a method of specifying the pH of the starting solution for preparing a capsule, which contains a dissolved state of native gellan gum and the polymer or copolymer, to 2 to 6, and drying the starting solution in the form of a capsule. The inventors conducted further research based on these findings and completed the present invention.

More specifically, the present invention provides, for example, the following hard capsules, starting solutions for preparing capsules, methods for producing hard capsules, and a hard capsule formulation.

[Item 1-A]

A hard capsule having a film comprising:

(A) a polymer or copolymer obtained by polymerizing or copolymerizing at least one polymerizable vinyl monomer represented by Formula (1):

$$H_2C=C(R^1)-COOR^2 \quad (1)$$

wherein $R^1$ represents hydrogen or methyl, and $R^2$ represents hydrogen or alkyl having 1 to 4 carbon atoms, in the presence of polyvinyl alcohol and/or a derivative thereof; and (B) native gellan gum.

[Item 1-B]

A hard capsule according to Item 1-A, wherein the film contains 100 parts by mass of (A) and 0.1 to 5 parts by mass of (B).

[Item 2-A]

A starting solution for preparing capsules, comprising:

(A) a polymer or copolymer obtained by polymerizing or copolymerizing at least one polymerizable vinyl monomer represented by Formula (1):

$$H_2C=C(R^1)-COOR^2 \quad (1)$$

wherein $R^1$ represents hydrogen or methyl, and $R^2$ represents hydrogen or alkyl having 1 to 4 carbon atoms, in the presence of polyvinyl alcohol and/or a derivative thereof; and (B) native gellan gum, wherein the starting solution has a pH value of 2 to 6.

[Item 2-B]

A starting solution for preparing capsules according to Item 2-A, containing 100 parts by mass of (A) and 0.1 to 5 parts by mass of (B).

[Item 3]

A process for producing hard capsules, comprising the step of:

drying the starting solution of Item 2-A or 2-B into a capsule shape to obtain hard capsules.

[Item 4]

A process for producing hard capsules, comprising the step of:

immersing a capsule-molding pin in the starting solution of 2-A or 2-B, withdrawing the capsule-molding pin from the starting solution, and drying the starting solution adhering to the capsule-molding pin to obtain a hard capsule.

[Item 5]

A hard capsule obtained through the process of Item 3 or 4.

[Item 6]

A hard capsule formulation obtained by filling the hard capsule of Item 1-A, 1-B, or 5 with at least one member selected from the group consisting of:

(a) polyethylene glycols having a weight average molecular weight of 2,000 or less, or derivatives thereof, (b) polyoxyethylene sorbitan fatty acid esters, (c) fatty acids having 6 to 12 carbon atoms or salts thereof, (d) polyoxyethylene castor oil, (e) diethylene glycol ether derivatives, (f) aliphatic alcohols having 6 to 12 carbon atoms, and (g) polyoxyethylene sorbitol fatty acid esters.

Advantageous Effects of Invention

The hard capsule of the present invention has excellent stability even when filled with a solvent for dissolving poorly soluble drugs, and also ensures excellent solubility, thereby reducing disintegration time. The hard capsule of the present invention also has excellent mechanical strength and suppresses film softening in a low-humidity environment. Furthermore, the hard capsule of the present invention maintains a low moisture content.

The present invention provides a hard capsule that can be filled with various types of pharmaceutical active ingredients previously considered unsuitable to be encapsulated, and that has excellent mechanical strength during storage. This enables various types of drugs (including poorly soluble drugs) to be encapsulated into hard capsules. Further, since the hard capsule of the present invention has excellent stability even when filled with a solvent for dissolving poorly soluble drugs, it contributes to, for example, improvement in capsule quality.

Further, by adopting the method of specifying the pH of the starting solution for capsule preparation to 2 to 6 and drying the starting solution in the form of a capsule, it is possible to obtain a hard capsule with further improved mechanical strength.

BRIEF DESCRIPTION OF DRAWINGS

FIG. 1 shows structural formulae of native gellan gum (lower formula) and deacylated gellan gum (upper formula), wherein M$^+$ represents a cation.

FIG. 2 schematically illustrates an impact strength testing machine for hard capsules.

DESCRIPTION OF EMBODIMENTS

Figure 1:
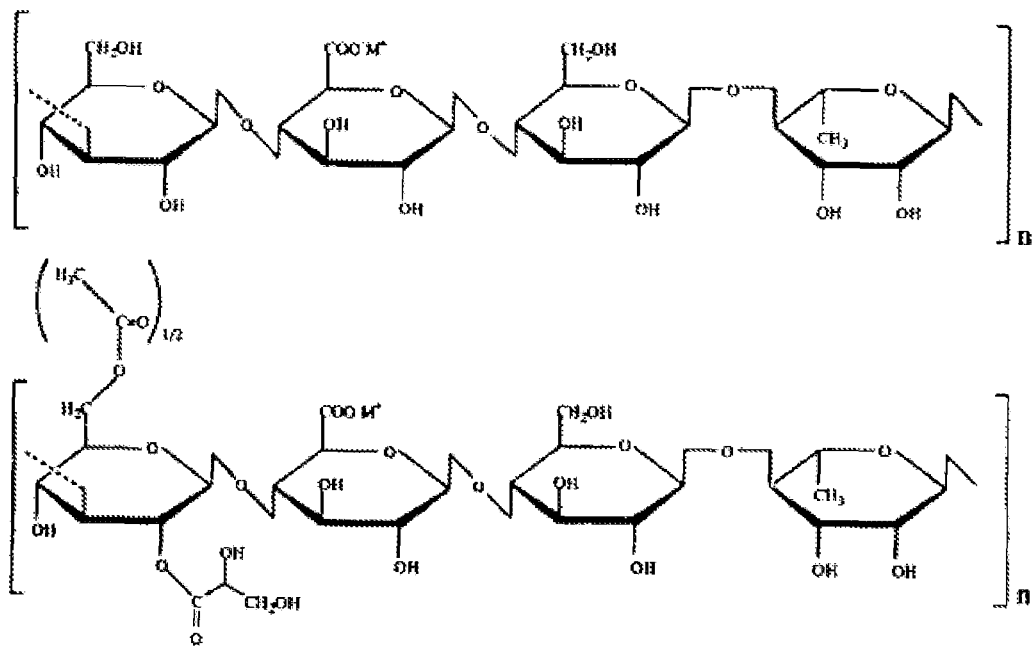
FIG. 1.

Hereinafter, the present invention is described in more detail.

1. Film

The film of the hard capsule of the present invention comprises (A) a polymer or copolymer obtained by polymerizing or copolymerizing at least one specific polymerizable vinyl monomer in the presence of polyvinyl alcohol and/or a derivative thereof, and comprises (B) native gellan gum.

(A) Polymer or Copolymer Obtained by Polymerizing or Copolymerizing at Least One Specific Polymerizable Vinyl Monomer in the Presence of Polyvinyl Alcohol and/or a Derivative Thereof Examples of polyvinyl alcohols (also referred to as PVA) and derivatives thereof usable in the present invention include completely saponified PVA, intermediately saponified PVA, partially saponified PVA, as well as various modified PVAs, such as amine-modified PVA, ethylene-modified PVA, or terminal-thiol-modified PVA.

PVAs can be obtained by radical-polymerizing vinyl acetate and suitably saponifying the obtained vinyl acetate. Therefore, PVAs generally have —OCOCH$_3$ groups that derive from vinyl acetate. PVAs can be classified into those that are completely saponified, intermediately saponified, partially saponified, and the like, depending on the degree of saponification. PVAs that are usable in the present invention preferably have a saponification degree of about 70 mol % or more, more preferably about 80 mol % or more, and further more preferably 85 mol % or more. Of these, saponificated PVAs with a saponification degree of 85 to 90 mol %, and in particular about 86 to 89 mol %, are preferable. As is well known in this field, PVA with a saponification degree of 98 mol % or more is generally regarded as completely saponified PVA; that is, completely saponified PVA does not necessarily mean a saponification degree of 100 mol %.

The aforementioned examples of modified PVAs, such as amine-modified PVA, ethylene-modified PVA, or terminal-thiol-modified PVA may be produced by, for example, methods known in this field.

Commercially available PVAs and derivatives thereof may also be used. They may be purchased from, for example, Nippon Synthetic Chemical Industry Co., Ltd., Japan Vam & Poval Co., Ltd., or the like.

PVAs are known to have various polymerization degrees. The average polymerization degree of PVA is not limited, and a PVA that is optimum in terms of concentration and viscosity is selected in accordance with its usage. Specifically, there are various methods for producing a hard capsule, as shown, for example, in "2. Production Method" below, and the optimum viscosity therefor depends on each of the methods. Accordingly, the polymerization degrees of usable PVAs and derivatives thereof are suitably selected. For example, PVAs usable in the present invention are those having an average polymerization degree of about 350 to 5000, and preferably about 1200 to 3800. This range of average polymerization degree is particularly preferable in hard capsule production using a dipping method.

PVAs and derivatives thereof may be used singly or in a combination of two or more. For example, PVAs having different degrees of saponification and various modified PVAs may be used singly or in a combination of two or more. Commercially available PVAs and derivatives thereof can also be used.

Polymerizable vinyl monomers usable in the present invention are compounds represented by Formula (1):

$$H_2C=C(R^1)—COOR^2 \qquad (1)$$

wherein $R^1$ represents hydrogen or methyl, and $R^2$ represents hydrogen or alkyl having 1 to 4 carbon atoms.

Specific examples of the polymerizable vinyl monomers usable in the present invention include acrylic acid, methacrylic acid, methyl methacrylate, methyl acrylate, ethyl methacrylate, ethyl acrylate, butyl methacrylate, butyl acrylate, isobutyl methacrylate, and isobutyl acrylate. Salts of acrylic acid or methacrylic acid can also be used. Examples of such salts include sodium salt, potassium salt, ammonium salt, and alkylamine salt.

The polymerizable vinyl monomers may be used singly or in a combination of two or more.

As the polymerizable vinyl monomers, it is preferable to use at least one of acrylic acid and methacrylic acid in combination with at least one member selected from the group consisting of methyl methacrylate, methyl acrylate, ethyl methacrylate, ethyl acrylate, butyl methacrylate, butyl acrylate, isobutyl methacrylate, and isobutyl acrylate. It is more preferable to use acrylic acid or methacrylic acid in combination with methyl methacrylate.

The ratio of the polyvinyl alcohol and/or derivative thereof to the polymerizable vinyl monomer in the polymer or copolymer (hereinafter also simply referred to as a PVA copolymer) obtained by polymerizing or copolymerizing at least one specific polymerizable vinyl monomer in the presence of polyvinyl alcohol and/or a derivative thereof is not particularly limited. However, it is preferable that the polyvinyl alcohol . and/or derivative thereof be used in an amount of 20 to 95 mass %, and the polymerizable vinyl monomer be used in an amount of 5 to 80 mass %. It is more preferable that the polyvinyl alcohol and/or derivative thereof be used in an amount of 50 to 90 mass %, and the polymerizable vinyl monomer be used in an amount of 10 to 50 mass %.

It is preferable that the PVA and/or derivative thereof be used in an amount of 20 mass % or greater, rather than less than 20 mass %, because when the amount of the PVA and/or derivative thereof is 20 mass % or greater, the produced capsule shows more improved dissolution or dispersion ability in water. In addition, it is also preferable that the polyvinyl alcohol and/or derivative thereof be used in an amount of 95 mass % or less, rather than more than 95 mass %, because when the amount of the PVA and/or derivative thereof is 95 mass % or less, the produced capsule is less susceptible to humidity, and so the capsule is not easily softened under high humidity.

When two or more polymerizable vinyl monomers are used in combination, the mixing ratio is not particularly limited. However, when at least one member selected from the group (I) consisting of acrylic acid, methacrylic acid and sodium salts, potassium salts, ammonium salts, and alkylamine salts thereof is used in combination with at least one member selected from the group (II) consisting of methyl methacrylate, methyl acrylate, ethyl methacrylate, ethyl acrylate, butyl methacrylate, butyl acrylate, isobutyl methacrylate, and isobutyl acrylate, the ratio thereof is as follows: the at least one member selected from the group (I) is preferably used in an amount of 5 to 50 mass % relative to 50 to 95 mass % of the member selected from the group (II), more preferably 10 to 40 mass % of the group (I) relative to 60 to 90 mass % of the group (II), further preferably 10 to 30 mass % of the group (I) relative to 70 to 90 mass % of the group (II), and further more preferably 10 to 20 mass % of the group (I) relative to 80 to 90 mass % of the group (II). Further, the mass ratio of (I) is preferably 5 to 50 mass o, more preferably 10 to 40 mass %, further preferably 10 to 30 mass %, and still further preferably 10 to 20 mass %, based on the total amount of the polymerizable vinyl monomers. Furthermore, the mass ratio of (II) is preferably 50 to 95 mass %, more preferably 60 to 90 mass %, further preferably 70. to 90 mass %, and still further preferably 80 to 90 mass %, based on the total amount of the polymerizable vinyl monomers.

A known method may be used for the polymerization or copolymerization. For example, it is possible to adopt a method of adding PVA and/or a derivative thereof to water, heating the mixture to effect dissolution, and adding at least one polymerizable vinyl monomer and a polymerization initiator thereto to initiate the copolymerization, thereby obtaining a resin. For example, PVA and/or derivative thereof is dispersed in ion exchange water and allowed to completely dissolve at 90 to 100° C. Then, at least one polymerizable vinyl monomer is added thereto, and after purging with nitrogen, a polymerization initiator is added to conduct a reaction for about 2 to 5 hours. The mass ratio of the PVA and/or derivative thereof to the polymerizable vinyl monomer in the PVA copolymer is determined according to the mass ratio of the PVA and/or derivative thereof to the polymerizable vinyl monomer added to water. Therefore, the mass ratio of the PVA and/or derivative thereof to polymerizable vinyl monomer in the PVA copolymer, as the amounts to be added to water, is preferably equal to the above-mentioned mass ratio in the PVA copolymer.

Usable polymerization initiators are those hitherto used. Examples thereof include 2,2'-azobis(2-amidinopropane) hydrochloride, AIBN (azoisobutyronitrile), and like azo compounds; potassium persulfate, sodium persulfate, ammonium persulfate, and like persulfates; t-butyl hydroperoxide and like organic peroxides; and hydrogen peroxide-tartaric acid, hydrogen peroxide-sodium tartrate, and like redox initiators.

The amount of the PVA copolymer of (A) in the film of a hard capsule is, on a dry mass basis, preferably about 70 to 99.9 mass %, more preferably about 80 to 99.8 mass %, and still more preferably about 85 to 99.7 mass %, relative to the total mass of the film.

According to the present invention, although restrictive interpretation is not intended, the reaction mechanism of the polymerization or copolymerization of at least one specific polymerizable vinyl monomer in the presence of polyvinyl alcohol and/or a derivative thereof is assumed to be as follows: first, a polymerization initiator abstracts hydrogen from the methyl group at the terminal of —OCOCH$_3$ present in the PVA, creating a radical. Then, the polymerizable vinyl monomer bonds to the radical, allowing the double bond of the polymerizable vinyl monomer to be cleaved, thereby again creating a radical. Then, the polymerizable vinyl monomer bonds to the radical, and the reaction is repeated in the same manner as above.

In the present invention, the PVA copolymer of (A) has a structure in which at least one kind of the aforementioned polymerizable vinyl monomers is graft-polymerized with —OCOCH$_3$, which is a side chain of PVA. In this graft polymerization, the PVAs may be joined together through a polymer obtained by polymerization or copolymerization of at least one kind of the polymerizable vinyl monomers. More specifically, the PVAs may be cross-linked through a polymer obtained by polymerization or copolymerization of at least one kind of the polymerizable vinyl monomers.

For example, when acrylic acid and methyl methacrylate are used as polymerizable vinyl monomers, the PVA copolymer of (A) has a structure in which a copolymer of acrylic acid and methyl methacrylate is bonded to PVA through —OCOCH$_3$ of the PVA. Specific examples of such PVA copolymers (copolymers of polyvinyl alcohol/acrylic acid/methyl methacrylate) include POVACOAT® Type R and POVACOAT® Type L (produced by Daido Chemical Corporation).

(B) Native Gellan Gum

The film of the hard capsule of the present invention further comprises (B) a compound of native gellan gum.

Gellan gum is obtained by subjecting a microorganism (*Pseudomonas elodea*), which is separated from a hydrophyte, to liquid culture, and collecting a gummy substance produced outside the cells in the culture solution. Deacylated gellan gum is obtained by deacylating the resulting gum, and native gellan gum is obtained by collecting the resulting gum without deacylation. The difference between deacylated gallan gum and native gallan gum is the presence/absence of acetyl and glyceryl in the 1,3-linked glucose. By removing this acetyl and glyceryl, deacylated gellan gum is obtained. FIG. 1 shows the reported primary structures of deacylated gellan gum and native gellan gum. The structural formulae in FIG. 1 are, however, shown for ease of understanding and not necessarily to limit the native gellan gum to the formula.

For the present invention, the native gellan gum collected through the culture of Pseudomonas elodea can be suitably used. It is also possible to purchase marketed native gellan gum, such as Kelco Gel CG-HA, Kelco Gel LT100, Kelco Gel HM, and Kelco Gel HT (all produced by CP Kelco).

Although it is not particularly limited, the native gellan gum used in the present invention preferably has a gel strength of 400 to 650 g/cm$^2$ measured under the following conditions.

Gel Strength Measurement Conditions 295 g of distilled water is placed in a weighed beaker, and 2.0 mL of 0.3 M $CaCl_2.2H_2O$ is added thereto. The mixture is stirred with a propeller agitator at 700±100 rpm. Then, 3.0 g of native gellan gum is added thereto, and the mixture is heated under stirring for 15 minutes to 94 to 95° C. This solution is mixed with distilled water at 95° C. to 300 g, and then it is placed in a TPA ring mold. The mold is covered with a lid and allowed to stand for 24 hours. The gel strength of the resulting gel is measured using a TA-TX2 Texture Analyzer at 20 to 21° C. with a Texture Technologies TA-19 plunger.

The amount of (B) native gellan gum contained in the film of a hard capsule may be appropriately adjusted according to the amount of (A) PVA copolymer. For example, to ensure desirable capsule film formation, the amount of native gellan gum is preferably, on the dry mass basis, about 0.05 to 10 mass %, more preferably about 0.1 to 5 mass %, further preferably about 0.2 to 3 mass %, and further more preferably about 0.2 to 1 mass %, based on the total mass of the film. By adjusting the amount of native gellan gum within this range, a capsule film can be desirably formed. It is also possible to prevent excessive increase in viscosity and thereby prevent defective film formation.

Further, the film of a hard capsule preferably contains 0.1 to 5 parts by mass, more preferably 0.3 to 2 parts by mass of (B) native gellan gum, based on 100 parts by mass of (A) PVA copolymer.

(C) Other Components

The film may also comprise other components in addition to (A) and (B) above insofar as the effect of the present invention is not impaired.

For example, the film may contain a known plasticizer. Examples of plasticizers include polyhydric alcohols. Specific examples of polyhydric alcohols include glycerol, ethylene glycol, diethylene glycol, triethylene glycol, polyethylene glycol, propylene glycol, polypropylene glycol, diglycerol, 1,3-butylene glycol, and sugar alcohols. Examples of sugar alcohols include sorbitol and mannitol. Of these, glycerol, propylene glycol, sorbitol, and mannitol are preferable, and glycerol and propylene glycol are more preferable. These may be used singly or in a combination of two or more.

The film may also contain an ester of polyhydric alcohol. As the esters of polyhydric alcohols, it is possible to use, for example, an ester of a polyhydric alcohol and a carboxylic acid having 1 to 5 carbon atoms, preferably 1 to 4 carbon atoms, and more preferably 1 to 3 carbon atoms. Preferable examples thereof include monoesters, diesters, triesters, etc., of the aforementioned polyhydric alcohols. Specific preferable examples of the esters of polyhydric alcohols include glycerol triacetate (hereinafter also referred to as "triacetin"), glycerol monoacetate, glycerol diacetate, glycerol tributyrate, glycerol tripropionate, propylene glycol diacetate, and ethylene glycol dibutyrate. Of these, triacetin is particularly preferable. These may be used singly or in a combination of two or more.

The film may also contain an ester of polyvalent carboxylic acid. As the esters of polyvalent carboxylic acids, it is possible to use, for example, an ester of a polyvalent carboxylic acid and alcohol having 1 to 5 carbon atoms, preferably 1 to 4 carbon atoms, and more preferably 1 to 3 carbon atoms. For example, monoesters, diesters, triesters, etc., of polyvalent carboxylic acids can be used. The usable polyvalent carboxylic acids are not limited as long as they have two or more carboxyl groups. Specific preferable examples of polyvalent carboxylic acids include citric acid, acetylcitric acid, tartaric acid, malic acid, fumaric acid, maleic acid, malonic acid, glutaric acid, adipic acid, and succinic acid. Specific preferable examples of the esters of polyvalent carboxylic acids include triethyl citrate, tributyl citrate, acetyl triethyl citrate, diethyl succinate, and dimethyl succinic acid. Of these, triethyl citrate is particularly preferable. These may be used singly or in a combination of two or more.

Further, to prevent softening of the film, a water-soluble polymer such as a cellulose derivative may also be incorporated in the film to an extent that does not impair the effects of the present invention. Examples of such water-soluble polymers include natural polysaccharides, semisynthetic polysaccharides, proteins, and synthetic polymers.

Examples of natural polysaccharides include agar, mannan, pullulan, starches (e.g., corn starch, potato starch, wheat starch, and rice starch), dextrin, pregelatinized starch, amylose, and dextran.

Examples of semisynthetic polysaccharides include cellulose-based polymer, hydroxypropyl starch, hydroxyethyl starch, and cyclodextrin polymers.

Examples of proteins include gelatin, casein, and zein.

Examples of synthetic polymers include polyvinyl pyrrolidone, polyoxyethylene polyoxypropylene glycols, carboxyvinyl polymers, and polyethylene glycols.

Examples of cellulose-based polymers include hydroxypropyl methylcellulose (also called hypromellose in the Japanese Pharmacopoeia; hereinafter also referred to as "HPMC"), hydroxypropyl cellulose (hereinafter also referred to as "HPC"), methylcellulose (hereinafter also referred to as "MC"), and hydroxyethylcellulose (hereinafter also referred to as "HEC").

These may be used singly or in a combination of two or more.

The film may also contain a gelling aid, if necessary. Although native gellan gel can be gelatinized without a gelling aid, addition of a gelling aid is conducive to increasing the gelatinization temperature. Examples of gelling aids include water-soluble compounds containing potassium ions, sodium ions, or calcium ions. Examples of such water-soluble compounds include potassium chloride, potassium phosphate, calcium chloride, and sodium chloride.

Further, as with general hard gelatin capsules or cellulose derivative capsules, the hard capsule of the present invention may contain a dye, a pigment, and like colorants; an opacifying agent; a flavor; sodium lauryl sulfate and like surfactants; and the like, within a range that does not hinder the effects of the present invention.

The amount of one or more of these other components (C) is suitably adjusted within a range that enables the production of the hard capsule.

The thickness of the film of the hard capsule is not particularly limited, as long as satisfactory functions of a hard capsule are ensured, and is generally about 0.01 to 5 mm, preferably about 0.05 to 1 mm, and more preferably about 0.05 to 0.5 mm.

The above film may also be used as a film of a soft capsule, as well as a film of a hard capsule.

2. Production Method

The hard capsule comprising the above film of the present invention may be produced by, for example, an injection molding method or a dipping method. The production method is not particularly limited to the above as long as a hard capsule can be formed. Methods that are used to produce general hard gelatin capsules may also be used. It is preferable to employ a dipping method. A dipping method utilizes the property of gelatinization of a hard capsule base solution due to temperature change.

An example of a production method for hard capsules according to the dipping method is given below. A molding pin is immersed in a solution (aqueous solution or gel) in which a composition containing (A) a polymer or copolymer obtained by polymerizing or copolymerizing at least one specific polymerizable vinyl monomer in the presence of polyvinyl alcohol and/or a derivative thereof, (B) native gellan gum, and optionally, (C) other components, is dissolved. The molding pin is then withdrawn from the solution, followed by gelling and drying the composition to form a film. Specifically, a capsule-molding pin is immersed in a solution (solution for preparing a capsule) in which (A) and (B) (and optionally, (C)) are dissolved. The capsule-molding pin is then withdrawn from the solution, and the solution (solution for preparing a capsule) adhering to the molding pin is dried to form a hard capsule film. The methods are exemplified more specifically described in the Examples.

3. Starting Solution for Preparing Capsule

The present invention also includes a starting solution for preparing a capsule. As described above, the hard capsule of the present invention having the above film can be produced from a starting solution for preparing a capsule. By drying the starting solution for preparing a capsule into a capsule shape, it is possible to produce a hard capsule of the present invention.

As described above, the starting solution (preferably an aqueous solution) for preparing a capsule contains (A) and (B) (and optionally, (C)), which are dissolved therein. The order of dissolving (A), (B), and (C) is not limited insofar as the starting solution for preparing a hard capsule of the present invention can be obtained. For example, it is possible to first dissolve (A) in water, and then dissolve (B) (and optionally, (C)). To dissolve (A) and (B) (and (C)) in water, the mixture may be stirred as required. Further, the water may be heated as required, preferably to about 80 to 100° C.

The concentrations of (A) and (B) (and optionally, (C)) in the starting solution for preparing a capsule are not limited and can be set appropriately insofar as the hard capsule of the present invention can be obtained. For example, the concentration of (A) is preferably 10 to 20 mass %, more preferably 12 to 18 mass %. The concentration of (B) is preferably 0.01 to 0.5 mass %, more preferably 0.03 to 0.3 mass %.

Further, in the starting solution for preparing a capsule, the amount of (B) native gellan gum is preferably 0.1 to 5 parts by mass, more preferably 0.3 to 2 parts by mass, based on 100 parts by mass of (A) PVA copolymer.

Furthermore, the pH of the starting solution for preparing a capsule is preferably about 2 to 6, more preferably about 3 to 5, and further more preferably about 3.5 to 4. If the pH of the starting solution for preparing a capsule falls out of the above range after (A) and (B) (and optionally, (C)) are dissolved, a pH adjuster may be added to control the pH. To increase the pH, alkaline substances such as an ammonium aqueous solution may be used. To decrease the pH, acidic substances such as citric acid or hydrochloric acid may be used. The strength of the hard capsule can be further improved by using such a starting solution for preparing a capsule having a specific range of pH.

4. Hard Capsule Formulation

The present invention also encompasses a hard capsule formulation obtained by filling the hard capsule having the above-described film with content.

There is no particular limitation on the form of contents used to fill the capsule, and the contents may be, for example, in the form of a liquid, a powder, granules, a paste, a semi-solid or ointment, or a cream. The capsule of the present invention is preferably used for encapsulating, in particular, a poor-solubility-drug-dissolving solvent.

As described above, a poor-solubility-drug-dissolving solvent refers to a solvent for dissolving a poorly soluble drug. Poorly soluble drugs refer to drugs having poor water solubility and may be any of those defined as "sparingly soluble", "slightly soluble", "very slightly soluble", or "practically insoluble or insoluble", as described in the Japanese Pharmacopoeia Fifteenth Edition. Specifically, the degree of dissolution within 30 minutes is evaluated by placing a drug in water (in the case of a solid drug, first processing the drug into powder), and then vigorously shaking the drug in water at 20±5° C. for 30 seconds at 5-minute intervals. When the amount of water required to dissolve 1 g or 1 mL of a drug is not less than 30 mL and is less than 100 ml, the drug is evaluated as "sparingly soluble"; when the amount is not less than 100 mL and is less than 1,000 mL, the drug is evaluated as "slightly soluble"; when the amount is not less than 1,000 mL and is less than 10,000 mL, the drug is evaluated as "very slightly soluble"; when the amount is not less than 10,000 mL, the drug is evaluated as "practically insoluble or insoluble".

There is no particular limitation on poor-solubility-drug-dissolving solvents as long as they are pharmaceutically acceptable and can dissolve poorly soluble drugs. Examples of poor-solubility-drug-dissolving solvents include polyethylene glycols and derivatives thereof, diethylene glycol ether derivatives, propylene glycol fatty acid esters, glycerin fatty acid esters, polyglyceryl fatty acid esters, polyoxyethylene glycerin fatty acid esters, sorbitan fatty acid esters, polyoxyethylene sorbitan fatty acid esters, polyoxyethylene sorbitol fatty acid esters, polyoxyethylene castor oil, medium-chain fatty acids and salts thereof, and medium-chain aliphatic alcohols.

As polyethylene glycols, those having a low molecular weight are preferable. Examples thereof include polyethylene glycols having a weight average molecular weight of 2,000 or less, preferably 1,500 or less, and more preferably 1,000 or less. Specific examples thereof include PEG 400 (a polyethylene glycol having a weight average molecular weight of about 400). Examples of polyethylene glycol derivatives include fatty acid ester derivatives (esters of polyethylene glycol and fatty acid). The weight average molecular weights of polyethylene glycols are measured in the following manner. 42 g of phthalic anhydride is added to a 1-L lightproof ground-in stopper bottle containing 300 mL of newly distilled pyridine. The mixture is vigorously shaken to effect dissolution, and then left to stand for 16 hours or more. Thereafter, 25 mL of the obtained liquid is introduced into a pressure-resistant ground-in stopper bottle (about 200 mL), followed by the addition of about 0.8 to 15 g of a target PEG sample. The resulting bottle is sealed, enclosed in durable fabric, and placed in a water bath that has been heated to 98±2° C. in advance so that the bottle is immersed therein. The bottle is kept in the bath for 30 minutes while the temperature is kept at 98±2° C., and then the bottle is taken out of the water bath and cooled in air to room temperature. Subsequently, 50 mL of 0.5 mol/L sodium hydroxide liquid is added thereto, followed by further addition of five drops of a pyridine solution of phenolphthalein (1→100). The resulting liquid is titrated with 0.5 mol/L sodium hydroxide liquid, provided that the titration is terminated when the liquid exhibits a pale red color continuously for 15 seconds. A blank experiment is carried out in a manner similar to the above. The weight average molecular weight is calculated using the following formula:

[Math. 1]

$$\text{Average molecular weight} = (\text{the amount of sample } (g) \times 4{,}000/(a\text{-}b))$$
$a$: the amount (mL) of 0.5 mol/L sodium hydroxide liquid consumed in the blank experiment $b$: the amount (mL) of 0.5 mol/L sodium hydroxide liquid consumed in the experiment of the PEG sample Examples of medium-chain fatty acids and salts thereof include fatty acids having 6 to 12 carbon atoms and salts thereof. Specific examples thereof include caproic acid, caprylic acid, capric acid, and lauric acid, and sodium salts and potassium salts of these acids.

Examples of medium-chain aliphatic alcohols include aliphatic alcohols having 6 to 12 carbon atoms. Specific examples thereof include caproyl alcohol, capryl alcohol, and lauryl alcohol.

The poor-solubility-drug-dissolving solvents can be used singly or in a combination of two or more.

Solvents to be filled in the hard capsule of the present invention are not limited to only poor-solubility-drug-dissolving solvents as long as they are pharmaceutically acceptable solvents capable of dissolving drugs. It is also possible to use a mixture of a poor-solubility-drug-dissolving solvent and one or more other known solvents.

It has been difficult to fill hitherto-known hard capsules with a poorly soluble drug dissolved in a solvent, because the poor-solubility-drug-dissolving solvent often induced capsule breakage or other defects. However, the hard capsule comprising the film of the present invention is not easily broken even when filled with a poor-solubility-drug-dissolving solvent; therefore, the present invention enables filling of the capsule with a poorly soluble drug that is dissolved in a solvent. Further, the hard capsule of the present invention exhibits an excellent low moisture property, compared with hitherto-known hard capsules. The term "low moisture property" refers to a property with low moisture content. When the film of a hard capsule has high moisture content, the moisture in the film migrates into the solvent contained in the capsule, possibly decreasing the stability of the drug and solvent. Therefore, it is preferable that hard capsules have a low moisture property. The excellent low moisture property can be confirmed by a desirable result of at least one measurement of the two moisture content comparison measurements under the condition of 25° C., 40% RH, and the condition of 25° C., 75% RH. It is more preferable to obtain desirable results in both of the measurements. "RH" denotes relative humidity.

The above-mentioned poor-solubility-drug-dissolving solvents may contain a thickener. By adding a thickener, for example, the following effects are obtained: the operation of filling the hard capsule with a solvent can be simplified, and leakage of the filled material from the hard capsule can be prevented. There are no particular limitations on thickeners, as long as they are pharmaceutically acceptable. Examples of the thickeners include light anhydrous silicic acid, vegetable oils, and cellulose derivatives (e.g., those described in pharmaceutical textbooks or those generally used). The amount of thickener added is preferably, for example, 0.1 to 10 parts by weight, more preferably 0.3 to 3 parts by weight, relative to 100 parts by weight of the poor-solubility-drug-dissolving solvent.

The above-mentioned poor-solubility-drug-dissolving solvent may further contain an additive that can generally be added to a solvent to be encapsulated, as long as such an additive does not impair the functions of the capsule. Examples of such additives include lactose and starches.

Drugs (including poorly soluble drugs) to be encapsulated into the hard capsule of the present invention are not limited due to the drug's application. As medicines, for example, the following can be encapsulated into the hard capsule of the present invention: vitamins, antifebriles, analgesics, antiphlogistics, antiulcer drugs, cardiotonics, anticoagulants, hemostatic agents, bone resorption inhibitors, vascularization inhibitors, antidepressants, antitumor agents, antitussives/expectorants, muscle relaxants; antiepileptics, antiallergic agents, antiarrhythmics, vasodilators, antihypertensive diuretics, diabetes drugs, antituberculous agents, hormonal agents, antinarcotics, antibacterials, antifungals, antivirals, and the like. When encapsulated, these medicaments may have a solid form (for example, in the form of powder or granules) or may be dissolved in a solvent.

Specific examples of the poorly soluble medicaments are shown below.

Antipyretic Agents, Analgesic Agents, and Antiinflammatory Agents

Examples of antipyretic agents, analgesic agents, and antiinflammatory agents include salicylic acid, sulpyrine, flufenamic acid, dichlofenac, indomethacin, atropine, scopolamine, morphine, pethidine, levorphanol, ketoprofen, naproxen, ibuprofen, oxymorphone, aspirin, aminopyrine, phenacetin, acetaminophen, phenylbutazon, ketophenylbutazone, mefenamic acid, bucolome, benzydamine, mepirizole, tialamide, tinoridine, Xylocaine, pentazocine, dexamethasone, hydrocortisone, prednisolone, azulene, isopropylantipyrine, sasapyrine, clofezone, etodolac, and salts thereof.

Tranquilizers

Examples of tranquilizers include diazepam, lorazepam, oxazepam, oxazolam, clotiazepam, medazepam, temazepam, fludiazepam, meprobamate, nitrazepam, chlordiazepoxide, etc.

Antipsychotic Agents

Examples of antipsychotic agents include chlorpromazine, prochlorperazine, trifluoperazine, sulpiride, clocapramine hydrochloride, zotepine, haloperidol, etc.

Antibacterial Agents

Examples of antibacterial agents include griseofulvin, lankacidins (J.Antibiotics, 38, 877-885 (1985)), azole-based compounds, such as 2-[(1R,2R)-2-(2,4-difluorophenyl)-2-hydroxy-1-methyl-3-(1H-1,2,4-triazole-1-yl)propyl]-4-[4-

(2,2,3,3-tetrafluoropropoxy)phenyl-3-(2H,4H)-1,2,4-triazolone, fluconazole, itraconazole, etc.; nalidixic acid, piromidic acid, pipemidic acid trihydrate, enoxacin, cinoxacin, ofloxacin, norfloxacin, ciprofloxacin hydrochloride, sulfamethoxazole-trimethoprim, etc.

Antibiotics

Examples of antibiotics include gentamycin, dibekacin, kanendomycin, lividomycin, tobramycin, amikacin, dibekacin, fradiomycin, sisomycin, tetracycline, oxytetracycline, rolitetracycline, doxycycline, ampicillin, piperacilin, ticarcillin, cephalotin, cefotiam, cefotiam hexetil, cefsulodin, cefmenoxime, cefmetazole, cefazolin, cefotaxime, cefoperazone, ceftizoxime, moxalactam, thienamycin, sulfazecin, azthreonam, amoxicillin, cephalexin, erythromycin, bacampicillin, minocycline, chloramphenicol, and salts thereof.

Antineoplastic Agents

Examples of antineoplastic agents include 6-O-(N-chloroacetyl carbamoyl) fumagillol, bleomycin, methotrexate, actinomycin D, mitomycin C, daunorubicin, adriamycin, neocarzinostatin, cytosine arabinoside, fluorouracil, tetrahydrofuryl-5-fluorouracil, picibanil, lentinan, levamisole, bestatin, azimexon, glycyrrhizin, HER2 inhibitor (heterocyclic compounds and the like disclosed in WO 01/77107, etc.), taxol, doxorubicin hydrochloride, etoposide, mitoxantrone, mesna, dimesna, aminoglutethimide, tomoxifen, acrolein, cisplatin, carboplatin, cyclophosphamide, lomustine (CCNU), carmustine (BCNU), etc.

Hypolipidemic Drugs

Examples of hypolipidemic drugs include clofibrate, 2-chloro-3-[4-(2-methyl-2-phenylpropoxy)phenyl]ethyl propionate (Chem. Pharm. Bull., 38, 2792-2796 (1990)), clinofibrate, cholestyramine, soysterol, tocopherol nicotinate, nicomol, niceritrol, probucol, elastase, etc.

Antitussive and Expectorants

Examples of antitussive and expectorants include ephedrine, methylephedrine, noscapine, codeine, dihydrocodeine, alloclamide, chlorfedianol, picoperidamine, cloperastine, protokylol, isoproterenol, salbutamol, thalline, bromhexine, carbocysteine, ethylcysteine, methylcysteine and salts thereof.

Muscle Relaxants

Examples of muscle relaxants include pridinol, tubocurarine, pancuronium, chlorphenesin carbamate, tolperisone hydrochloride, eperisone hydrochloride, tizanidine hydrochloride, mephenesin, chlorzoxazone, phenprobamate, methocarbamol, chlormezanone, pridinol mesilate, afloqualone, baclofen, dantrolene sodium, etc.

Antiepileptic Agents

Examples of antiepileptic agents include phenytoin, ethosuximide, acetazolamide, chlordiazepoxide, phenobarbital, carbamazepine, primidone, etc.

Antiulcer Agents

Examples of antiulcer agents include lansoprazole, metoclopramide, famotidine, omeprazole, sulpiride, trepibutone, cetraxate hydrochloride, gefarnate, irsogladine maleate, cimetidine, ranitidine hydrochloride, nizatidine, roxatidine acetate hydrochloride, etc.

Antidepressants

Examples of antidepressants include imipramine, clomipramine, noxiptiline, phenelzine, etc.

Antiallergic Drugs

Examples of antiallergic drugs include diphenhydramine, chlorpheniramine, tripelenamine, methodiramine, clemizole, diphenylpyraline, methoxyphenamine, clemastine fumarate, cyproheptadine hydrochloride, mequitazine, alimemazine tartrate, etc.

Cardiotonic Drugs

Examples of cardiotonic drugs include trans-pi-oxocamphor, terenol, aminophylline, etilefrine, etc.

Antiarrhythmic Agents

Examples of antiarrhythmic agents include propranolol, alprenolol, bufetolol, oxprenolol, procainamide hydrochloride, disopyramide, ajmaline, quinidine sulfate, aprindine hydrochloride, propafenone hydrochloride, mexiletine hydrochloride, etc.

Vasodilator Drugs

Examples of vasodilator drugs include oxyfedrine, diltiazem, tolazoline, hexobendine, bamethan, nifedipine, nilvadipine, isosorbit dinitrate, diltiazem hydrochloride, trapidil, dipyridamole, dilazep hydrochloride, verapamil, nicardipine hydrochloride, ifenprodil tartrate, cinepazide maleate, cyclandelate, cinnarizine, pentoxifylline, etc.

Antihypertensive and Diuretic Agents

Examples of antihypertensive and diuretic agents include hexamethonium bromide, pentolinium, mecamylamine, ecarazine, clonidine, diltiazem, nifedipine, furosemide, trichlormethiazide, methyclothiazide, hydrochlorothiazide, hydroflumethiazide, ethiazide, cyclopenthiazide, florothiazide, ethacrynic acid, etc.

Antidiabetic Agents

Examples of antidiabetic agents include glymidine, glipizide, phenformin, buformin, metformin, glibenclamide, tolbutamide, etc.

Antitubercular Agents

Examples of antitubercular agents include isoniazid, ethambutol, para-aminosalicylic acid, etc.

Antinarcotics

Examples of antinarcotics include levallorphan, nalorphine, naloxone, and salts thereof.

Hormonal Drugs

Examples of hormonal drugs include steroid hormones, such as dexamethasone, hexestrol, methimazole, betamethasone, triamcinolone, triamcinolone acetonide, fluocinolone acetonide, prednisolone, hydrocortisone, estriol, etc.

Osteochondropathy Prevention and Treating Agents

Examples of osteochondropathy prevention and treating agents include prostaglandin Al derivative, vitamin D derivatives, vitamin K2 derivatives, eicosapentaenoic acid derivatives, benzylphosphonate, bisphosphonic acid derivatives, sex-hormone derivatives, phenolsulfophthalein derivatives, benzothiopyran or benzothiepine derivatives, thienoindazole derivatives, menatetrenone derivatives, helioxanthin derivatives and like non-peptidic osteogenesis-promotion enhancers; peptidic osteogenesis-promotion enhancers; etc.

Articular disorder treatment agents

Examples of articular disorder treatment agents include p38MAP kinase inhibitors (e.g., thiazole-based compounds and the like disclosed in WO 00/64894, etc.), matrix-metalloprotease inhibitors (MMPI), prednisolone, hydrocortisone, methylprednisolone, dexa/betamethasone, betamethasone and like anti-inflammatory steroid drugs; indomethacin, diclofenac, loxoprofen, ibuprofen, piroxicam, sulindac and like non-steroidal anti-inflammatory drugs; etc.

Hydrochlorides for Use in Treating Pollakiuria

Examples of hydrochlorides for use in treating pollakiuria include flavoxate, oxybutynin hydrochloride, terodiline hydrochloride, etc.

Antiandrogenic Agents

Examples of antiandrogenic agents include oxendolone, allylestrenol, chlormadinone acetate, gestonorone caproate, osaterone acetate, flutamide, bicalutamide, etc.

Fat-Soluble Vitamin Agents

Examples of fat-soluble vitamin agents include vitamins K1, K2, K3, K4 and like vitamin K, folic acid (vitamin M), etc.

Vitamin Derivatives

Examples of vitamin derivatives include 5,6-trance-cholecalciferol, 2,5-hydroxycholecalciferol, 1-[alpha]-hydroxycholecalciferol and like vitamin D3 derivatives; 5,6-trance-ergocalciferol and like vitamin D2 derivatives; etc.

Others

Examples of other poorly soluble medicaments include hydroxycam, diacerein, megestrol acetate, nicergoline, and prostaglandins.

In particular, included are acridine, ajmaline, amobarbital, chlordiazepoxide, chlormadinone acetate, clonazepam, diazepam, diltiazem, kitasamycin, dicumarol sulfathiazole, medazepam, menadione, midecamycin, piroxicam, nystatin, phenacetin, phenobarbital, phenothiazine, flunitrazepam, prednisolone, nicergoline, phenytoin, probucol, nifedipine, reserpine, furosemide, glibenclamide, indomethacin, griseofulvin, nitrazepam, albendazol, carbamazepine, and phenylbutazone are included.

These poorly soluble drugs are only examples, and the present invention is not limited to the aforementioned drugs.

Although a drug is dissolved in a poor-solubility-drug-dissolving solvent in a capsule in the above example, it is also possible to encapsulate a drug that is not poorly soluble. Commercially available products or those produced by a known method may be used as such drugs.

It is also possible to employ other known capsule techniques to the hard capsule formulation of the present invention, as required. For example, if the area where the cap and body of a capsule meet is sealed with, for example, a material similar to the coating film of the capsule, leakage or dissipation of the content can be prevented. The sealing can also be made using polyvinylpyrrolidone. Specific examples of sealing methods include a band-sealing method.

The hard capsule of the present invention can be used as an inhalation preparation or a pharmaceutical preparation for rectal administration in addition to use as a pharmaceutical preparation for oral administration. Further, in addition to drugs for medical treatment, the hard capsule of the present invention can also be used in the fields of, for example, food and cosmetics. Specifically, oral cosmetics or food may be encapsulated into the capsule of the present invention.

MODE FOR CARRYING OUT THE INVENTION

Hereinafter, the present invention is described in more detail with reference to Examples and Comparative Examples. However, the present invention is not limited to the following Examples.

In the Examples and Comparative Examples, "%" represents "mass %" unless otherwise specified. Further, "RH" denotes relative humidity. The term "addition concentration" in the tables represents the mass of the gelling agent (κ-carrageenan, native gellan gum, or deacylated gellan gum), relative to the total mass of the film.

EXAMPLES

1. PVA Copolymer 122 g of PVA (type: EG-25; average polymerization degree: 1,700; saponification degree: 88%; produced by Nippon Synthetic Chemical Industry Co., Ltd.) and 648 g of ion exchange water were placed in a separable flask equipped with a cooling reflux condenser, a dropping funnel, a thermometer, a nitrogen inlet tube, and a stirrer. First, PVA was dispersed at an ordinary temperature, and then completely dissolved at 95° C. Subsequently, 3.8 g of acrylic acid and 26.6 g of methyl methacrylate were added thereto. After the flask was purged with nitrogen, the temperature was increased to 50° C. Thereafter, 8.5 g of tertiary butyl hydroperoxide and 8.5 g of sodium erythorbate were added thereto. The reaction was terminated after 4 hours, thereby obtaining a PVA copolymer aqueous solution. The obtained PVA copolymer aqueous solution was used in the following experiments.

The pH of the PVA copolymer aqueous solution was 4.0. The solution was further mixed with ammonia water to prepare solutions having pH values of 5.2 or 5.5. The solution was also mixed with citric acid to prepare a solution having a pH value of 3.5. These solutions were also used in the following experiments.

2. Production of Hard Capsule (1) 0.36 g of κ-carrageenan as a gelling agent and 0.36 g of potassium chloride as a gelling aid were added to a solution obtained by adding 47 g of purified water to 153 g of the PVA copolymer aqueous solution (pH value=5.2), thereby preparing a starting solution for preparing capsules. The starting solution was heated to about 65° C. A stainless steel pin at room temperature was immersed and withdrawn to thereby produce a size No. 3 hard capsule having a film thickness of about 0.06 to 0.15 mm. This hard capsule was designated as "Comparative Example 1."

A size No. 3 hard capsule has a capacity of 0.3 mL, a weight of 0.05 g, a major axis of 1.6 cm, and a minor axis of 0.6 cm.

(2) Another capsule of the same size was produced in the same manner as in (1), except that a PVA copolymer aqueous solution having a pH value of 4.0 was used instead of the PVA copolymer aqueous solution having a pH value of 5.2. This hard capsule was designated as "Comparative Example 2".

(3) A hard capsule of the same size was produced in the same manner as in (1), except that κ-carrageenan and potassium chloride were not added and 0.12 g of native gellan gum (KELCOGEL CG-HA native gellan gum produced by CP Kelco) as a gelling agent was added to a solution prepared by adding 51 g of purified water to 149 g of the PVA copolymer aqueous solution (pH value=5.2) used in (1), thereby preparing a starting solution for preparing capsules. This hard capsule was designated as "Example 1".

(4) Another hard capsule of the same size was produced in the same manner as in (3), except that a PVA copolymer aqueous solution having a pH value of 4.0 was used instead of the PVA copolymer aqueous solution having a pH value of 5.2. This hard capsule was designated as "Example 2".

(5) Another hard capsule of the same size was produced in the same manner as in (4), except that a PVA copolymer aqueous solution having a pH value of 3.5 was used instead of the PVA copolymer aqueous solution having a pH value of 4.0. This hard capsule was designated as "Example 3".

(6) Another hard capsule of the same size was produced in the same manner as in (4), except that 1.0 g of deacylated gellan gum (KELCOGEL CG-LA gellan gum produced by CP Kelco) was used as a gelling agent instead of the native gellan gum. This hard capsule was designated as "Comparative Example 3".

3. Production of Film (1) A solution obtained by adding 63 g of purified water to 137 g of the PVA copolymer aqueous solution having a pH value of 5.5 was dropped on a glass plate, thereby producing a film having a thickness of about 100 micrometer. This film was designated as "Reference Example 1".

(2) A solution obtained by adding 63 g of purified water to 137 g of a PVA copolymer aqueous solution having a pH value of 4.0 was dropped on a glass plate, thereby producing a film having a thickness of about 100 micrometer. This film was designated as "Reference Example 2".

4. Evaluation Test (1) Hard Capsule Disintegration Test

Six of the respective capsules obtained in Examples and Comparative Examples were each filled with 0.2 mL of polyethylene glycol having a weight average molecular weight of 400 (hereinafter referred to as "PEG 400"). Each capsule was band-sealed using the PVA copolymer aqueous solution. The times consumed until the capsules opened were measured in accordance with the disintegration test method in the Japanese Pharmacopoeia 15th edition. The test was performed using water as a test liquid, and an auxiliary disk. The opening of each capsule was determined when the leakage of PEG 400 from the capsule was detected. Table 1 shows the result. In Table 1, "pH value" denotes the pH value of the starting solution for preparing capsules, and "gelling agent concentration (%) in capsule film" denotes a concentration of the gelling agent (mass %) in the capsule film. The "gelling agent concentration ((%) in capsule film)" was calculated based on the amount of starting materials and corresponds to the proportion of the gelling agent in the capsule film based on dry mass conversion. In addition, "gelling agent concentration ((%) in the starting solution)", which is the concentration of the gelling agent in the starting solution for preparing capsule, is also shown in the right column of Table 1.

TABLE 1

| Capsules | pH | Gelling Agent (and Gelling Aid) | Concentration of Gelling Aid (in capsule film (%)) | Time Consumed to Open capsule film (min) | Concentration of Gelling Aid (in Starting Solution (%)) |
|---|---|---|---|---|---|
| Comparative Example 1 | 5.2 | κ-carrageenan, KCl | 1.2 | 2.1 | 0.18 |
| Comparative Example 2 | 4.0 | κ-carrageenan, KCl | 1.2 | 1.7 | 0.18 |
| Example 1 | 5.2 | Native Gellan Gum | 0.4 | 1.4 | 0.06 |
| Example 2 | 4.0 | Native Gellan Gum | 0.4 | 1.3 | 0.06 |
| Example 3 | 3.5 | Native Gellan Gum | 0.4 | 1.7 | 0.06 |
| Comparative Example 3 | 4.0 | Deacylated Gellan Gum | 3.3 | 8.9 | 0.5 |

The result revealed that the time consumed until the capsule opened was short when the hard capsule contained native gellan gum as a gelling agent. Accordingly, it was found that this hard capsule ensures quick disintegration, i.e., superior solubility.

(2) Impact Strength Test for Hard Capsule

Figure 2:
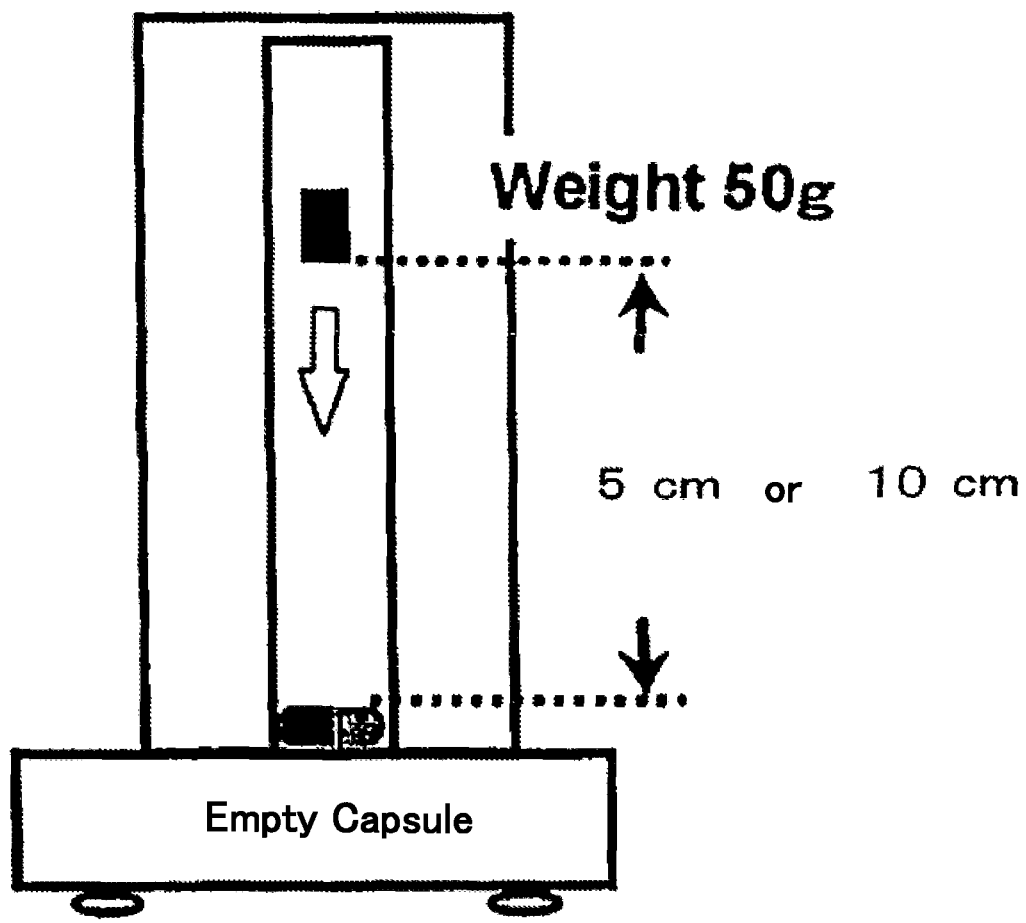
FIG. 2.

The capsules obtained in Examples and Comparative Examples were measured for impact strength after storage in a thermo-hygrostat for a week at 25° C., 40% RH, using an impact strength testing machine (a capsule hardness tester; Qualicaps Co., Ltd.) shown in FIG. 2. Specifically, a 50-g weight was vertically dropped from 5 cm or 10 cm above individual empty capsules, and the number of damaged capsules and the breakage rate (%) were found. The weight used in the test was a rectangular solid (height: 4 cm; width: 1.5 cm; and depth: 3 cm). The damage (breakage) of the capsule was determined based on the cracking of a capsule confirmed by visual inspection. Table 2 shows the results.

The proportion (%) of damaged capsules was calculated according to the following formula.

Breakage Rate (%)=(number of damaged capsules/number of specimens)×100

TABLE 2

| Capsule | Impact Strength 5 cm (number of damaged capsules/number of specimens) | Breakage Rate 5 cm (%) | Impact Strength 10 cm (number of damaged capsules/number of specimens) | Breakage Rate 10 cm (%) |
|---|---|---|---|---|
| Comparative Example 1 | 8/10 | 80 | 10/10 | 100 |
| Comparative Example 2 | 3/9 | 33 | — | — |
| Example 1 | 7/14 | 50 | 5/5 | 100 |
| Example 2 | 0/5 | 0 | 5/11 | 45 |
| Example 3 | 0/5 | 0 | 0/7 | 0 |
| Comparative Example 3 | 4/6 | 67 | 3/3 | 100 |

A comparison between Examples 1 to 3 revealed that when native gellan gum was used, easy breakage of capsules can be suppressed by decreasing the pH of the starting solution for preparing capsules. Further, a comparison between Comparative Example 1 and Comparative Example 2 revealed that easy breakage of capsules can be suppressed by decreasing the pH of the starting solution also for a capsule containing κ-carrageenan.

On the other hand, a comparison between Example 2 and Comparative Example 3 revealed that suppression of easy breakage of capsules was more significant in a capsule containing native gellan gum than a capsule containing deacylated gellan gum. This shows that a capsule containing a high-acyl gellan gum has a greater capsule strength.

(3) Moisture Value of Hard Capsule

After the above hard capsules were stored for a week at 25° C., 40% RH and at 25° C., 75% RH, 3 of them were each subjected to moisture value measurement in accordance with the loss on drying test in the Japanese Pharmacopoeia 15th edition. Specifically, the capsules were separated into caps and bodies to be subjected to mass measurement. Then, the capsules were dried in a dryer at 105° C. for 2 hours and cooled within a desiccator (silica gel) to be subjected to mass measurement again. The moisture value was then found from the mass difference of each capsule before and after drying. More specifically, using the mass difference before and after drying as a moisture mass, the ratio (%) of the moisture mass to the mass of capsule before drying was calculated as a moisture value.

Table 3 shows the result.

TABLE 3

| Capsule | Moisture Value (%) 40% RH | Moisture Value (%) 75% RH |
|---|---|---|
| Comparative Example 1 | 4.4 | 12.4 |
| Comparative Example 2 | 4.6 | 12.1 |
| Example 1 | 4.0 | 11.2 |
| Example 2 | 4.0 | 11.0 |
| Example 3 | 3.9 | 11.7 |
| Comparative Example 3 | 4.3 | 11.4 |

A hard capsule containing native gellan gum as a gelling agent had a lower moisture value than a hard capsule containing κ-carrageenan. More specifically, it was revealed that a hard capsule made of a capsule film containing native gellan gum (in particular, a hard capsule produced from a starting solution for preparing capsules having a pH value of about 2 to 6) showed more desirable low moisture content.

(4) Stability Test for Capsule Filled with Solvent

Three of the capsules obtained in Examples and Comparative Examples were each filled with 0.2 mL of polyethylene glycol having a weight average molecular weight of 400 (hereinafter referred to as "PEG 400"), and each capsule was band-sealed using the PVA copolymer aqueous solution produced in the above section "1. PVA copolymer". Then, the capsules were stored for 7 days at 40° C. while airtight-stoppered, and changes in appearance, such as a change in the capsule shape, and leakage, as well as the presence of cracking, were visually observed, so as to examine the stability of the capsules when filled with a solvent. Polyethylene glycol has a property of dissolving a poorly soluble drug. Filling a hitherto known capsule (e.g., a gelatin capsule) with polyethylene glycol has posed the problem that the moisture in the capsule film would migrate into the polyethylene glycol, causing breakage of the capsule.

The capsule appearance was evaluated in accordance with the following criteria:
a: No change in appearance
b: Slight change in appearance, but no practical problem
c: Significant change in appearance and practical use not possible

TABLE 4

| Capsule | Stability when filled with solvent | |
| --- | --- | --- |
| Comparative Example 1 | Appearance | Leakage of PEG 400 (number of capsules with PEG leakage/number of specimen) |
| Comparative Example 2 | a | 0/3 |
| Example 1 | a | 0/3 |
| Example 2 | a | 0/3 |
| Example 3 | a | 0/3 |
| Comparative Example 3 | a | 0/3 |

As is evident from the test results, an appearance change or a crack was hardly observed in the capsule of the present invention even when the capsule was filled with PEG 400. Accordingly, it was confirmed that the capsule of the present invention is completely usable as a practical drug formulation. Further, the results of Comparative Examples 1 to 3 confirmed usability of the capsules containing κ-carrageenan or deacylated gellan gum filled with PEG 400.

(5) Condition of Hard Capsule under High Humidity

After the above hard capsules were stored for a week at 25° C., 75% RH, the capsules were subjected to hardness evaluation with three panelists. The evaluation was made based on 4 levels (0 to 3) of hardness, and the total score was calculated for each capsule. More specifically, the panelists held the capsules in their fingers and evaluated the hardness based on the feel. The evaluation was performed using three specimens, the aforementioned 4 levels, and the three panelists. A perfect score was 27. A higher score indicates greater hardness. A lower score indicates more advanced softening. Table 5 shows the results.

TABLE 5

| Capsule | Hardness under 75% RH (score) |
| --- | --- |
| Comparative Example 1 | 3 |
| Comparative Example 2 | 6 |
| Example 2 | 15 |

As shown in Table 5, it was confirmed that capsule softening under high humidity was significantly suppressed in the capsule containing native gellan gum instead of κ-carrageenan.

(6) Tensile Strength Test of Film

After the films obtained in Reference Example 1 and Reference Example 2 were stored for three days at 25° C., 40% RH, a 1.5 cm×15 cm test specimen was cut out from each film to be subjected to measurement of tensile strength and film extension degree upon film breakage using a tensile strength tester. Table 6 shows the results. The tensile strength test was performed in accordance with JIS K 7127-1999 Plastics—Determination of tensile properties—Part 3: Test conditions for films and sheets. The test speed was 100 rum/min. Five test specimens were used.

TABLE 6

| Film | pH | Tensile Strength (MPa) | Extension Degree (%) |
| --- | --- | --- | --- |
| Reference Example 1 | 5.5 | 106 | 2.3 |
| Reference Example 2 | 4.0 | 88 | 2.7 |

As shown in Table 6, it was found that the PVA copolymer film having a smaller pH value had a greater film extension degree. Accordingly, it was assumed that a hard capsule using this PVA copolymer would not easily break.

The invention claimed is:

1. A hard capsule having a film comprising:
   (A) a polymer or copolymer obtained by polymerizing or copolymerizing, in the presence of polyvinyl alcohol and/or a derivative thereof, at least one polymerizable vinyl monomer represented by Formula (1):

$$H_2C=C(R^1)-COOR^2 \quad (1)$$

wherein $R^1$ represents hydrogen or methyl, and $R^2$ represents hydrogen or alkyl having 1 to 4 carbon atoms; and
   (B) native gellan gum,
   wherein the film contains 0.05 to 10 mass % of (B) based on the total mass of the film, on a dry mass basis.

2. A process for producing the hard capsule of claim 1, comprising the step of:
   drying a starting solution into a capsule shape to obtain hard capsules,
   wherein the starting solution comprises:
   (A) a polymer or copolymer obtained by polymerizing or copolymerizing, in the presence of polyvinyl alcohol and/or a derivative thereof, at least one polymerizable vinyl monomer represented by Formula (1):

$$H_2C=C(R^1)-COOR^2 \quad (1)$$

wherein $R^1$ represents hydrogen or methyl, and $R^2$ represents hydrogen or alkyl having 1 to 4 carbon atoms; and
   (B) native gellan gum,
   wherein the starting solution has a pH value of 2 to 6.

3. A process for producing the hard capsule of claim 1, comprising the step of:
   immersing a capsule-molding pin in a starting solution, withdrawing the capsule-molding pin from the starting solution, and drying the starting solution adhering to the capsule-molding pin to obtain a hard capsule, wherein the starting solution comprises:

(A) a polymer or copolymer obtained by polymerizing or copolymerizing, in the presence of polyvinyl alcohol and/or a derivative thereof, at least one polymerizable vinyl monomer represented by Formula (1):

$$H_2C=C(R^1)-COOR^2 \qquad (1)$$

wherein $R^1$ represents hydrogen or methyl, and $R^2$ represents hydrogen or alkyl having 1 to 4 carbon atoms; and (B) native gellan gum, wherein the starting solution has a pH value of 2 to 6.

4. A hard capsule formulation obtained by filling the hard capsule of claim 1 with at least one member selected from the group consisting of:

(a) polyethylene glycols having a weight average molecular weight of 2,000 or less, or derivatives thereof, (b) polyoxyethylene sorbitan fatty acid esters, (c) fatty acids having 6 to 12 carbon atoms or salts thereof, (d) polyoxyethylene castor oil, (e) diethylene glycol ether derivatives, (f) aliphatic alcohols having 6 to 12 carbon atoms, and (g) polyoxyethylene sorbitol fatty acid esters.

5. The hard capsule according to claim 1, wherein the film contains 0.1 to 5 parts by mass of (B) based on 100 parts by mass of (A).

* * * * *